United States Patent
Fitzpatrick et al.

(10) Patent No.: US 9,315,849 B2
(45) Date of Patent: Apr. 19, 2016

(54) METHODS AND COMPOSITIONS FOR ESTIMATING SOIL MICROBIAL LOAD

(71) Applicant: Prolific Earth Sciences Corporation, Englewood, NJ (US)

(72) Inventors: Judith Fitzpatrick, Englewood, NJ (US); James Sottilo, Miller Place, NY (US); Austin Lin, New York, NY (US); Brady Trexler, Hasbrouck Heights, NJ (US)

(73) Assignee: Prolific Earth Sciences Corporation, Englewood, NJ (US)

( * ) Notice: Subject to any disclaimer, the term of this patent is extended or adjusted under 35 U.S.C. 154(b) by 0 days.

(21) Appl. No.: 14/242,652

(22) Filed: Apr. 1, 2014

(65) Prior Publication Data
US 2014/0220623 A1    Aug. 7, 2014

Related U.S. Application Data

(60) Provisional application No. 61/849,964, filed on Feb. 6, 2013.

(51) Int. Cl.
| | | |
|---|---|---|
| *C12Q 1/06* | (2006.01) | |
| *C12Q 1/04* | (2006.01) | |
| *C12Q 1/24* | (2006.01) | |
| *G01N 15/06* | (2006.01) | |
| *G01N 15/00* | (2006.01) | |

(52) U.S. Cl.
CPC .. *C12Q 1/06* (2013.01); *C12Q 1/24* (2013.01); *G01N 15/06* (2013.01); *G01N 2015/0061* (2013.01); *G01N 2015/0693* (2013.01)

(58) Field of Classification Search
CPC .................................. C12Q 1/06; C12Q 1/04
See application file for complete search history.

(56) References Cited

U.S. PATENT DOCUMENTS 3,171,801 A * 3/1965 Rice et al. ............... 210/725

OTHER PUBLICATIONS

Hill et al. (Methods for assessing the composition and diversity of soil microbial communities. Applied Soil Ecology 15 (2000) 25-36).*
Nel et al. (A turbidimeter for measuring soil-particle concentration in suspensions. 1987 South African Journal of Plant and Soil. South African Journal of Plant and Soil, 4:2, 90-93).*
Wilson et al. (Water Quality Notes: Water Clarity (Turbidity, Suspended Solids and Color. Department of Soil and water Science 2010, pp. 1-8).*
Bakken, "Separation and purification of bacteria from soil", Appl Enviro Microbial., 49(6):1482-7 (1985).
Bending, et al, "Microbial and biochemical soil quality indicators and their potential for differentiating areas under contrasting agricultural management regimes", Soil Biol. BioChem., 36:1785-92 (2004).
Brinton, "Compost Quality in America", Compost Quality Standards & Guidelines Report, Woods End Research Laboratory, Inc. (2000).
Brinton, et al., "Compost sampling for nutrient and quality parameters: variability of sampler, timing and pile depth", Compost Sci Utilization., 20(3):141-9 (2012).
Czaczyk, et al., "Changes in cell number and the ATP content during the composting process", Polish J Enviro Studies, 10(3):149-53 (2001).
Dreyer and Gardner, "A general method of estimating the relative turbidity or opacity of fluid suspensions including bacterial emulsions", Biochem. J.,10 (3):399-407 (1916).
Egamberdiyeva, "The effect of plant growth promoting bacteria on growth and nutrient uptake of maize in two different soils", Applied Soil Ecology, 36:184-9 (2007).
Ekelund, et al., "Distribution with depth of protozoa, bacteria and fungi in soil profiles from three Danish forest sites", Soil Biol Biochem., 33:475-81 (2001).
Fredslund, et al., "Development and application of a most-probable-number-PCR assay to quantify flagellate populations in soil samples", Applied and Enviro Microbial., 67(4):1613-8 (2001).
Gans, et al., "Computational improvements reveal great bacterial diversity and high metal toxicity in soil.", Science, 309:1387-90 (2005).
Garrcia-Gil, et al., "Long term effects of municipal solid waste compost application on soil enzyme activities and microbial biornass", Soil Biol. Biochem., 32:1907-13 (2000).
Holmes and Zak, Soil microbial biomass dynamics and net nitrogen mineralization in northern hardwood ecosystms, Soil Sci Soc Am J., 58:238-43 (1994).
Hoorman and Islam, "Understanding soil microbes and nutrient recycling", Fact Sheet, Ohio State University, (2010).
Ingham, et al., "Interactions of bacteria, fungi, and their nematode grazers: effects on nutrient cycling and plant growth", Ecological Monographs, 55 (1):119-40 (1985).
Lugtenberg, et al., "Microbe-plant interactions: principles and mechanisms" Antonie van Leeuwenhoek, 81:373-83 (2002).
Martens, "Current methods for measuring microbial biomass C in soil: potentials and limitations", Biology Fertility of Soils, 19(2-3):87-99 (1995).
Martin and Brathwaite, "Compost and compost tea: principles and prospects as substrates and soil-borne disease management strategies in soil-less vegetable production", Biological Agriculture Horticulture, 28(1):1-33 (2012).

(Continued)

*Primary Examiner* — Karen Cochrane Carlson
*Assistant Examiner* — Natalie Moss
(74) *Attorney, Agent, or Firm* — Pabst Patent Group LLP (57) ABSTRACT

Methods and compositions for the preparation of soil samples and the determination of the number of microbes within a soil sample are disclosed. The methods include measuring, solubilizing, bleaching and filtering soil samples and measuring the turbidity of the filtered solution. The turbidity of the sample can be determined by visual inspection of a Secchi disk viewed through the column liquid sample in a transparent tubular cylinder, or by using a cell phone camera and application. Devices and kits for the rapid, cost efficient determination of microbial numbers in the field setting are disclosed. The disclosed devices and methods can also be used for applications other than determination of microbial numbers.

22 Claims, 3 Drawing Sheets

(56) References Cited

OTHER PUBLICATIONS

Mestre, "A precision photometer for the study of suspensions of bacteria and other microorganisms", J Bacteriology, 30(4):335-58 (1935).

Roesch, et al., "Pyrosequencing enumerates and contrasts soil microbial diversity" ISME J., 1:283-90 (2007).

Schloss and Handelsman, "Toward a census of bacteria in soil", PLoS Comput Biol., 2(7):e92. (2006).

Shrestha, et al., "Microblally enhanced compost extract: does it increase solubilisation of minerals and mineralization of organic matter and thus Improve plant nutrition", Bioremediation and Biodegradation, 3(5):1-9 (2012).

Suzuki, et al, "DAPI direct counting underestimates bacterial abundances and average cell size compared to AO direct counting", Am Soc Limnology Oceanography, 38(7):1566-70 (1993).

Torsvik, et al., "High diversity in DNA of soil bacteria", Appl. Enviro. Microbiol., 56(3):782-7 (1990).

Valpassos, et al., "Effects of soil management systems on soil microbial activity, bulk density and chemical properties", Pesquisa Agropecuaria Brasileira, 36(12):1539-45 (2001).

Van Veen and Paul, "Conversion of biovolume measurements of soil organisms, growth under various moisture tensions, to biomass and their nutrient content"., Applied and Enviro Microbiology, 37(4):686-92 (1979).

Van Veen, et al., "Fate and activity of microorganisms introduced into soil", Microbiol Molecular Biology Rev., 61(2):121-35 (1997).

Witt, et al., "A rapid chloroform-fumigation extraction method for measuring soil microbial biomass carbon and nitrogen in flooded rice soils", Biol. Fertility Soils, 30(5-6):510-9 (2000).

* cited by examiner

METHODS AND COMPOSITIONS FOR ESTIMATING SOIL MICROBIAL LOAD

CROSS-REFERENCE TO RELATED APPLICATIONS

This application claims the benefit of and priority to U.S. Ser. No. 61/849,964 filed Feb. 6, 2013, which is incorporated by reference in its entirety.

STATEMENT REGARDING FEDERALLY SPONSORED RESEARCH OR DEVELOPMENT

The United States Government has certain rights to this invention by virtue of support from National Science Foundation Grant No. 0903168.

FIELD OF THE INVENTION

The field of the invention generally relates to methods and kits containing compositions for preparing soil or compost samples and means for measurement of the microbial content of soil and compost, as well as other analytes of interest.

BACKGROUND OF THE INVENTION

Measurement of microbial biomass or other soil analytes is difficult because of the large amount of particulate matter that is irrelevant to the measurement of these analytes and because the color of an extract precludes assaying for analytes by methods such as spectrophotometery, turbidity, nephalometry and visual comparison. One of the most difficult parameters to measure is Microbial Biomass which is an excellent indicator of soil and compost quality and is a predictor of soil fertility. Soil microbes recycle the organic matter in soil and convert it into forms that can be utilized by plants. Bacteria represent the majority of the microbial life in soil and serve as the bottom rung of the microbial soil food chain which consists of bacteria, fungi, protozoa, algae and nematodes. Abundant microbial life indicates that the nutrient levels of soil are sufficient and balanced and that there is an absence of significant levels of deleterious or poisonous substances such as heavy metals or high concentrations of salts.

Studies have revealed that the ratios and diversity of the various microorganisms present in soil varies with different soil types and is a predictor of soil fecundity. However, tests and test standardization to establish the microbial content of soils have not been extensively developed (Compost Quality in America, Woods End Research Laboratory, Inc., Report (2000)).

Currently, several laboratories provide commercial in-house services to estimate the numbers of various different types of microbes in soil. These estimates are based upon laboratory tests that are costly, labor intensive and results are not available for 7-21 days. Because only about 10% of soil microbes can be cultured and then only with great difficulty and time, analyses must be performed by direct counting using a microscope and a diluted sample on a slide. The slide can be difficult to read because soil particles predominate, and expertise is required to distinguish between bacteria, fungi and protozoa, rendering these tests prohibitively expensive for use as routine quality control. In addition, soil samples must be transported to the laboratory for analysis and it can take days or weeks for the results to be reported. These methods are not practical for estimation of the microbial content of composts and compost extracts, which must be used within one or two days of formulation. Further, the results are not consistant from lab to lab, due to the subjective nature of visual counts.

Bacteria are typically the most abundant and diverse microbial component of soil. A Standard laboratory technique for quantitation of bacteria is based upon spectrophotometric measurement of turbidity within a solution. However, this method is problematic for measurement of the bacterial content of soil samples because the particles and pigments in soil also contribute to turbidity, reflectance and/or transmittance measurements. In addition, many microbes in soil are firmly attached to the soil particles and do not readily go into solution. Further, it is not practical to apply these methods to a field test to assess microbial biomass in soil because of the need for a turbidometer or spectrophotometer which would require calibration, precluding rapid and efficient use in the field. Accurate estimates of microbial numbers are required on-site and within a few minutes of sampling to determine whether a new treatment increased microbial growth or how much to dilute a compost extract.

Therefore it is an object of the invention to provide methods and reagents for measuring the microbial content of soil that are convenient for use in the field setting.

It is a further object of the invention to provide time effective and cost effective methods for providing an estimate of microbial numbers within a soil sample.

SUMMARY OF THE INVENTION

Methods and compositions can be used to measure the microbial content of soil based upon turbidity, reflectance, and/or transmittance of bacteria in solution. These methods enable rapid measurements without the need for advanced expertise or laboratory equipment. The number of microbes measured using the methods are not statistically different from those estimated by counting or spectrophotometric measurement of transmittance or absorbance. These methods are more accurate than classical methods, such as titration plating of bacterial cultures which may detect less than 10-12% of the microbes present.

Methods for measuring the number of microbes in a sample of soil include separating the microbes from the soil particles using a solubilizing agent and shaking (hereafter referred to as solubilizing), filtering the microbial solution, bleaching pigments in the microbial solution, measuring the turbidity of the filtered microbial solution and calculating the number of microbes in solution based upon the turbidity, reflectance, and/or transmittance. Exemplary soil samples include earthy soil or compost, liquid compost extract, or liquid compost tea and other microbial soil amendments. The microbes can be solubilized using physical methods of agitation such as shaking. Shaking in the presence of a detergent or other releasing agent enhances solubilization of the microbes. Preferred detergents are polyether modified polysiloxane added to a concentration of 0.01% or 0.1% TWEEN® 20. In some embodiments the solubilized microbial solution are filtered using two or more different sized filters in succession to progressively remove smaller particulate material from the solution. In one embodiment a 100-1000 micrometer filter is used, followed by a 5 micrometer filter. In another embodiment, the filter is a fiberglass plug of between 200 and 600 mg, preferably 500 mg, for a standard 15 ml centrifuge tube holding 10 ml of reaction solution. Methods of compensating for pigments by bleaching of the microbial solution are also provided. Bleaching agents can include dilute sodium hypochlorite. NaOCl (CLOROX® Regular Bleach) or chlorine dioxide. A preferred final concentration of chlorine dioxide is 75 ppm. A preferred clarification agent is a saturated solution of Chlorine dioxide in a dropper bottle. The Chlorine dioxide can be provided in granular form (like that for swimming pools), which is stable for an extended period when reconstituted by the user in a chemically resistant container. A preferred method is to provide a premixed solution of clarifying and releasing agent consisting of 75 ppm Chlorine Dioxide and 0.1% TWEEN® in the reaction vial.

Methods of measuring the turbidity, reflectance and/or transmittance of filtered microbial solutions are provided. In some embodiments the turbidity of the filtered microbial solution is measured using a turbidity tube and a Secchi disk, or any method or device that resembles or utilizes the same principles as the Secchi disc for measuring turbidity (i.e., correlates color with measurements based upon standardized controls). In other embodiments the turbidity of the solution is determined by spectrophotometry, nephalometery or reflectometry. Devices for measuring turbidity, reflectance and/or transmittance are also disclosed. A preferred device is the portable SOIL BIOMETER™ turbidity tube. Turbidity tubes can include a transparent cylindrical vessel, such as a 10 ml glass measuring cylinder. One end of the vessel includes an opening and the opposing end is closed and connected to a support stand. The closed end can be transparent, or can include a pattern of opposing colors that is visible from above by looking through the open end of the tube, or a separate color schedule. The transparent cylindrical vessel includes markings to allow measurement of the fluid within the vessel by the height of the fluid column. In a preferred embodiment the pattern of opposing colors is a Secchi disk.

Kits including devices for measuring the turbidity, reflectance and/or transmittance of a solution are also disclosed. Typically kits contain a turbidity tube and/or cell phone app for reading reflected light with instructions as well as the reagents and apparatus required to determine the number of bacteria in a soil sample. Kits can include a turbidity tube and one or more of a syringe, a syringe filter with a 5 micrometer sieve size, a tube filter with a 100 micrometer sieve size, a measuring cup with a capacity of 0.2-0.4 ml of soil when fully packed, or a 3 ml syringe modified for use as a punch with plunger which allows measurement of soil volume by the gradations on the syringe, and direct insertion into the reaction vial, a vial containing detergent releasing agent, an anti-foaming agent, a bleaching agent tablet, a reaction vial, a pipette and one or more Secchi disks. In some embodiments, kits also contain a portable automated shaker device, such as the small Robart shaker or a battery operated vibrating wand, such as can be constructed using an ORAL B® childrens tooth brush base with a plastic probe attached for penetrating the reaction vial.

Kits can include a turbidity tube or Cell phone with an application for estimation of microbial number; a measuring device such as a punch with plunger or a cup that delivers a discrete volume of soil (for 10 ml of test solution the test requires between 0.2 and 0.8 ml of solid earth); a dropper bottle containing detergent releasing agent/an anti-foaming agent; a tablet or dropper bottle containing a bleaching agent; or 10 ml of test solution containing clarifying and releasing agent in the reaction vial, a reaction vial, a fiberglass filter plug and a pipette. In some embodiments kits also contain a portable automated shaker device, such as the small Robart shaker or a battery operated vibrating wand, such as can be constructed using an ORAL B® children's tooth brush base with a plastic straw attached for penetrating the reaction vial.

DETAILED DESCRIPTION OF THE INVENTION

I. Definitions

The terms "soil" and "soil sample" as used herein, refer to any earthy mix of minerals, air, water, and organic matter. Soils include composts, compost extracts and compost teas and microbial soil amendments.

"Compost extract" refers to a solution prepared by mixing compost and water and removing most of the solid residual. "Compost tea" refers to a compost extract fortified with other nutrients, such as organic and/or inorganic fertilizer.

The term "microbes" refers to microscopic organisms such as bacteria, fungi, algae and protozoa.

The terms "microbial biomass", "microbial content" and microbial number" refer to the amount of microorganisms in a given habitat. Microbial biomass, content or numbers can be expressed either as the weight of organisms per unit area or as the volume or number of organisms per unit volume of habitat or solution.

The term "Secchi disk" refers to a pattern of contrasting colors, typically black and white. Secchi disks are used to visually determine the transparency of fluids, such as water in lakes, etc. The depth of fluid at which the pattern of colors on the disk is no longer apparent is a function of the turbidity of the fluid. Other patterns that rely on discriminating pattern such as those used with the Mc Farland Standards are also known and can be used.

The term"filtrate" refers to soluble soil samples that have been passed through one or more filters.

The term "the field" refers to the location of origin of a sample, such as the geographic location at which a given sample is obtained. Typically, the term refers to a non-laboratory setting.

II. Methods of Measuring Soil Microbes

A test has been established that can be utilized to rapidly measure the microbial content of a soil sample in the field setting. In one embodiment of these methods, trademarked as the SOIL BIOMETER™ test, the turbidity, reflectance and/or transmittance of soil microbes in water can be used to estimate the number of microbes less than 5 or 10 micrometers in diameter. To use turbidity, reflectance and/or transmittance as an indicator of microbial content, microbes in the sample are detached from soil by shaking in the presence of water containing a releasing agent and/or bleaching agent. The mixture is then filtered to remove all particles >5 or 10 micrometers in diamete and the turbidity of the eluent is determined using a Secchi disk viewed through a column of eluent in a turbidity tube. The SOIL BIOMETER™ test gives results in less than 5 minutes, can be performed in the field and does not require specialized skills or training.

A. Preparation of Samples

Methods for determining the microbial content of soils require the preparation of soil samples. Sample preparation involves the measurement of samples, detachment of microbes from soil particles and removal of pigments and particulates that can interfere with the measurement of turbidity, reflectance, and/or transmittance.

1. Obtaining Samples

Samples of solid soil can be collected and measured in the field using a soil collection device and/or measuring cup or a 3 ml syringe modified for use as a punch with plunger which allows measurement of soil volume by the gradations on the syringe, and direct insertion into the reaction vial. In some embodiments, multiple samples of equal volume are taken across a certain area and combined in a clean mixing vessel to produce a composite sample. In other embodiments, a sample is obtained by inserting a collection device into a batch of solid compost or soil.

Solid soil samples can be measured using a collection vessel of a known volume. In one embodiment, solid soil is packed into a measuring vessel, such as a cup washer, to a volume of 0.210 ml. Alternatively, a punch with plunger and defined volume can be used to deliver from 0.2-0.8 ml of sample. Measurement of sample by volume corrects for soil water content. The volume of the cup washer is 0.21 ml, i.e., it holds 210 microliters of water. As can be seen in Table 1, a soil sample can hold more than 2× dry weight of soil before volume changes.

TABLE 1

Soil Volume as Function of Water Content

| µls water added | Weight Sample 1 | Weight Sample 2 | |
|---|---|---|---|
| 0 | 0.98 | 0.132 | |
| 25 | 0.103 | 0.155 | |
| 25 | 0.124 | 0.177 | |
| 25 | 0.146 | 0.201 | |
| 25 | 0.172 | 0.223 | |
| 25 | 0.197 | 0.257 | water seeped out bottom |
| | 0.2197 | | |
| | 0.24 | | water seeped out bottom |

Measuring volume compensates for water content of sample. The sample can hold more than 2× dry weight of soil before volume changes.

Liquid soil samples, such as compost extract or compost tea, can be collected and measured by filling a clean collection vessel of a known volume using the BIOMETER™ or a pipette. Preferably the liquid soil has been homogenized or thoroughly mixed prior to sample acquisition. Approximately 1-2 mL of a liquid sample can be obtained using a measuring pipette or using the cap of a reaction vial that contains approximately 2 mL of liquid soil when completely filled. The percentage of solid earth/compost can be 2-8% to water.

Solid and liquid samples are placed into a clean reaction vial. Solid samples that have been measured in a measuring cup can be transferred into the vial within the cup. Samples taken by punch can be directly delivered into the reaction tube by depressing the plunger. Liquid samples that have been measured using a pipette or the cap of the reaction vial can be introduced into the vial by inverting the cap over the opening of the vial.

2. Solubilizing Soil Samples

Soil samples are solubilized within the reaction vial by addition of water followed by physical agitation to release soil-associated microbes into solution. If desired, releasing agents, clarification agents or anti-foaming agents are also added at this point. The amount of releasing agent, clarification agent or anti-foaming agent added to a soil sample can vary depending on the nature of the soil sample and the desired results.

a. Releasing Agents

Releasing agents enable or enhance the solubilization of microbes within a soil sample by increasing dissociation of the microbes from soil particles. Releasing agents for use in the methods do not cause extensive foaming of the solution that would interfere with filtration and/or measurement of turbidity, reflectance and/or transmittance. Releasing agents for use in the methods are non-toxic and do not affect the visualization or measurement of microbes within the time required for analysis or for several hours afterward. In addition, preferred releasing agents are stable for extended periods of time and can be packaged and stored in a ready-to-use form.

Mild detergent releasing agents are disclosed. Exemplary detergents include blends of polyether-polymethylsiloxane-copolymer and nonionic surfactant, or polyether modified polysiloxane (CAPSIL®), TWEEN® 20, TWEEN® 80, also referred to as polysorbate 20 or 80, dioctanoylphosphatidyl choline and polyethylene-polypropylene glycol. In a preferred embodiment the releasing agent is either 0.1% TWEEN® 20 or CAPSIL®. CAPSIL® can be a liquid at a 0.1%, 1%, 10%, 50% or 100% formulation in a dispensing vial. A preferred test concentration of CAPSIL® is 0.2% b. Clarifying Agents

Clarifying agents are disclosed. Solubilized soil samples containing humic acid can be dark brown in color. Clarifying agents neutralize the pigmentation of soluble soil samples to facilitate accurate measurements of turbidity, reflectance and/or transmittance. Preferred clarifying agents for use in the methods do not affect the visualization or measurement of microbes within the time required for analysis or for several hours afterward. Exemplary clarifying agents are hydrogen peroxide, chlorine dioxide, or mixtures of sodium hypochlorite, sodium chloride, sodium carbonate, sodium hydroxide and sodium polyacrylate (i.e., CLOROX® Regular Bleach). Numerous clarifying agents are commercially available. In addition to clarifying activity, hydrogen peroxide ($H_2O_2$) in commercial bleaches contributes to the separation of particulates. In a preferred embodiment, the clarifying agent is chlorine dioxide at a final concentration of 50-150 ppm or CLOROX® at a final concentration of 10%. A formulation that is preferred because it is extremely stable, commercially available to the public and can be sent by mail is the granulated form sold for use in the maintenance of swimming pools. 5 drops of a saturated solution of this is sufficient to clarify a 10 ml test solution. Granules can be provided in a non-polyethylene dropper bottle: Approximately 100 mg of granules in a 15 ml vial can be reconstituted by adding approximately 15 ml of tap water. The solution is stable for more than a month. In a preferred embodiment 10 mL of a premixed solution of clarifying and releasing agent consisting of 75 ppm Chlorine Dioxide and 0.1% TWEEN® 20 is provided in the reaction vial.

Clarifying agents are preferably safe for use by consumers and for mailing. In a preferred embodiment the clarifying agent is added to a concentration of about 50-150 ppm final $ClO_2$ concentration or final CLOROX® concentration of 10% (i.e., a concentration 100 times that used for the routine purification of drinking water). In a preferred embodiment, the clarifying agent is available in a stabilized, premeasured and individually packaged form, such as tablets or granules, that are used for water purification or as 10 mL of a premixed solution of clarifying and releasing agent consisting of 75 ppm Chlorine Dioxide and 0.1% TWEEN 20 in the reaction vial. Typically, clarifying agents do not cause any damage to microbes in the time it requires to perform the methods and measurements of the test.

3. Anti-Foaming Agents

Anti-foaming agents or "defoamers" are also disclosed. Anti-foaming agents act by decreasing the surface tension of gas bubbles and reducing foam. Exemplary anti-foaming agents include alcohols, stearates, insoluble oils, polydimethylsiloxanes, other silicones and glycols. Anti-foaming agents can prevent the formation of foam or can be added to disperse a foam that has formed. Anti-foaming agents can be added as a measured amount of dry powder, or as a tablet. A preferred anti-foaming agent is poly(dimethylsiloxane), the silicon dioxide simethicone. A preferred concentration of simethicone is 125 milligrams of simethicone in a volume of 25 mL or 5 milligrams per mL solution. In some embodiments an anti-foaming agent is present in the composition of a detergent, such as CAPSIL®.

In a particular embodiment, a clarifying agent is added to a final concentration of about 50-150 ppm or final CLOROX® concentration of 10%. In one embodiment, a single tablet containing a suitable amount of a clarification agent, such as chlorine dioxide is added to the soil sample in the reaction vial. The tablet form of chlorine dioxide can be broken before addition to the tube to facilitate solubilization of the tablet. The tablet formulation is utilized at 100 times the concentration used for purification of water. In a preferred embodiment, 10 mL of a premixed solution of clarifying and releasing agent consisting of 75 ppm $ClO_2$ and 0.1% TWEEN® 20 is provided in the reaction vial.

In further embodiments, a releasing agent such as CAPSIL® is added to the soil sample in the reaction vial. In a preferred embodiment, CAPSIL® is added to a final concentration of 0.2%. CAPSIL® is a 100% active blend of organo-silicone and non-ionic surfactants that enables solutions to spread, sold by Aquatrols, NJ. CAPSIL® is not stable when diluted in clarifying reagent but 0.1% TWEEN® gives the same result and is stable in the diluted reagent.

In one embodiment a single tablet of a clarification agent and a single, measured drop of releasing agent are added to 200 ml-400 ml of solid soil or 2 mL of compost extract in the reaction vial immediately prior to the addition of water and shaking. In another embodiment, 5×50 µl drops of a saturated solution of Chlorine Dioxide and a 20 µl single drop of CAPSIL® are added to 200-400 ml of solid soil or 1-2 mL of liquid soil in the reaction vial immediately prior to the addition of 10 ml water and shaking. In a preferred embodiment, 10 mL of a premixed solution of clarifying and releasing agent consisting of 0.08 mg/mL Chlorine Dioxide and 0.1% TWEEN® 20 is provided in the reaction vial.

Anti-foaming agents can be used to prevent or reduce the formation of bubbles resulting from agitation. Anti-foaming agents such as the silicon dioxide simethicone can be added according to the requirements of the sample. In one embodiment simethicone is added to a final concentration of 5 milligrams per ml. Anti-foaming agents can be added prior to shaking to prevent formation of foam, or can be added after shaking to disperse foam that has formed, according to the requirements of the sample.

The mixture of soil samples including releasing agents, clarification agents and/or anti-foaming agents are solubilized by the addition of tap water to the reaction vial. In one embodiment, water is added to the reaction vial to a total volume of 10 mL. Water can also be added to a total volume of less than 10 mL, such as to make a total volume of 1 mL, 2 mL, 3 mL, 4 mL, 5 mL, 6 mL, 7 mL, 8 mL or 9 mL, according to the requirements of the operator. Sufficient water can also be added to a final volume of more than 10 mL, such as to up to 25 mL, or more than 25 mL.

Immediately following the addition of water, the reaction vial cap is screwed onto the vial and the contents are mixed by vigorous agitation. Agitation can be manual (i.e., shaking by hand, for example, in a vertical and/or horizontal plane), or can be assisted by the use of an automated agitation device, such as a vortex shaker ("vortexing"), sonication or a device similar to a ROBART® Shaker device or by a vibrating probe.

The amount of agitation required to dissociate microbes from soil particles can vary depending upon the nature and quantity of the sample and depending upon the method of shaking Vigorous shaking by hand for 10 to 20 minutes can be sufficient to release microbes from 200-400 ml of solid soil or 2 mL of liquid soil into 10 ml of solution in the absence of releasing agent. In the presence of a releasing agent such as 0.2% CAPSIL® 5-20 minutes of agitation by hand shaking or 1 minute of agitation using a ROBART® shaker, or 10-20 seconds of a vibrating probe should be sufficient to release the microbes from 0.2-0.5 ml of solid soil or 1-2 mL of liquid soil.

Immediately following agitation the vial is placed vertically in a rack with the cap facing upwards. The cap is removed from the reaction vial and the solution is allowed to settle for 10-30 seconds.

3. Filtering Solubilized Soil Samples

Solubilized soil samples are filtered to remove non-microbial particulate matter on the basis of size. The filtration of liquid samples to remove particulate matter is a standard and well-known technique and can be carried out by any means known in the art. The limitation in filtering is finding filter materials that do not absorb microbes. Most filter materials tested absorbed 40-60% of a microbial suspension. The least retention was found by using a fiberglass plug. In certain embodiments filtering methods are established by Biometer measured turbidity before and after filtration and/or microscopic evaluation of the solution after each filtration step, to ascertain that the number of microbes in the final filtrate correlates with that in the starting sample. Filtration methods can be optimized on a sample-by-sample basis to enhance the accuracy of results for microbial size. In preferred embodiments, filtration removes cellulosic and other materials but preserves the entire microbial population less than 10 µm.

The one or more filtering steps do not require extensive technical expertise and take less than 10 minutes. The solubilized soil sample may be filtered in stages, first by using a coarse filter and then using a finer filter. In preferred embodiments the soil solution is passed through a coarse pre-filter to remove larger particles, such as those with a diameter of more than 100 micrometers. The coarse pre-filter can be attached to one end of an open tube-filter device that can be pushed into the reaction vial, capturing the filtrate in the tube. This filtrate can then be passed through a fine filter to exclude particles more than 5 or 10 micrometers in size.

In one embodiment, a coarse filter is attached to a tube filter, such as a serum separator, which is inserted into the reaction vial and the settled soil solution is filtered by pushing the tube filter slowly down the length of the reaction vessel. The coarse-filtered soluble soil sample is then introduced into the barrel of a syringe fitted with a fine filter. The syringe is then placed over the opening of a collection vessel, such as a glass graduated cylinder. The solution is filtered through the fine filter by inserting the plunger into the barrel of the syringe and forcing the plunger down the barrel. The expelled solution contains no particulate matter above the size determined by the specifications of the filter. In some embodiments, a portion or all of the filtered soil solution can be passed through a succession of filters of different pore sizes, to enable the quantitation of microbes of corresponding sizes. For example, to estimate the number of bacteria as compared to the number of protozoa and nematodes, bacteria smaller than 2 micrometers can be separated from protozoa and nematodes using a filter with a 2 micrometer sieve size.

In a preferred embodiment, a fiberglass (commercial insulation grade) plug of 250-750 mg replaces a series of filters. The fiberglass plug is inserted into the reaction vial after shaking and is slowly depressed using a straw or any other device. The resulting eluent is substantially clear of cellulosic material.

B. Measurement of Turbidity, Reflectance and/or Transmittance

The turbidity, reflectance and/or transmittance of the clarified, filtered sample is measured to indicate the bacterial concentration of the soil sample. Turbidity can be measured at the site of sample acquisition using a SOIL BIOMETER™ turbidity tube, which utilizes a variation of the Secchi tube principle or cell phone camera. Turbidity, reflectance and/or transmittance can also be measured in the laboratory using an instrument such as spectrophotometer, reflectometer or nephalometer or using a cell phone camera and app to measure absorbance, reflectance or nephalometric parameter.

1. Measurement of Microbes in Soil Samples

To measure turbidity using the SOIL BIOMETER™ the filtered soil sample is introduced into the open end of the 10 ml graduated cylinder or similarly constructed tube called a Biometer™. The turbidity of the fluid in the vessel is measured by visual perception of a Secchi disk pattern through the column of fluid in the vessel.

In some embodiments, the narrow glass tube is placed directly over a black and white pattern (or any pattern that allows discrimination) that is obscured by fluid at a certain turbidity. To visually measure turbidity the operator looks through the open end of the narrow glass tube to inspect the bottom. Sufficient fluid should be introduced into the glass vessel to obscure the visual discrimination of the pattern. Fluid is then carefully removed from the glass tube using a pipette until discrimination of the pattern is possible. The height of the fluid column at which the pattern becomes obscured by turbidity is then determined from markings on the side of the glass. Estimation of the number of microbes of a certain size per mL of solution can be determined by reference to a chart such as Table 2:

TABLE 2

Reference chart for estimating bacterial number from fluid volume using the SOIL BIOMETER ™ turbidity tube.

| SOIL BIOMETER ™ Reading (in mL) | Estimated number of bacteria < 5 μm in size (in millions) in one capful or 1 mL of compost extract/tea | Estimated number of bacteria < 5 μm in size (in millions) in two capfuls or 2 mL of compost extract/tea |
|---|---|---|
| 2.0 | 200 | 100 |
| 2.5 | 100 | 50 |
| 4.0 | 50 | 25 |
| 7.0 | 25 | 12.5 |
| 10 | 10 | 5 |

In addition, other methods of measuring turbidity/reflectance/transmittance, such as using a spectrophotometer, a reflectometer and/or commercially available calibration standards, such as the Mc Farland Standards, can be utilized to measure bacterial concentration within the filtered soil solutions.

In some embodiments, methods of enhancing turbidity/reflectance/transmittance, such as the addition of coagulating agents, can be used to increase the sensitivity of the test.

2. Other Measurements

The methods for clarifying a soil sample can also be applied to measurement of other soil properties. Samples can be useful for purposes such as estimating nitrogen or phosphorus concentrations using colorimetric methods, or for immunoassays or enzyme assays of soil components such as fungi. In some embodiments, solutions such as eluent from filtered solubilized soil samples can be analyzed for the presence of nitrogen. Nitrogen can be detected and measured using any of the available methods for determination of protein, nitrates or nitrites, or amino sugars. In a particular embodiment, the methods for the SOIL BIOMETER™ test can be used to produce eluent for the bicinchoninic acid assay (BCA assay) for determining the total concentration of protein in a solution. The BCA assay can readily be carried out using samples prepared by the described methods due to the stability of the reagents and the test's insensitivity to interfering substances such as detergents and pH. In other embodiments the eluent produced by the described methods can be easily adapted to testing for contaminants such as metals or poisons such as pesticides and fecal bacteria in addition to the identification of native soil microbes. For example, fungi can be detected by the presence of markers such as chitin or ergosterol in the eluent using any of the many immunoassay or affinity methods known in the art. In a particular embodiment, the amount of chitin or ergosterol in a soil sample solution correlates with the mass of fungi in the sample. This can be measured by capture of chiten using a lectin with detection by visualization by labeled lectin. The filtrate produced enables testing of all analytes that require soil filtrate with the characteristics described herein.

III. Devices for Measuring Soil Microbes

Kits containing devices and reagents for the quantitation of microbes in soil samples are disclosed. The devices and reagents can be in a portable kit for use in the field setting. Devices for the preparation of soil samples include bleaching agents, separating agents, anti-foaming agents and filtration devices. Devices for measuring turbidity/reflectance/transmittance, such as the SOIL BIOMETER™ turbidity tube with Secchi like disks and cell phone app are also disclosed.

Figure 1A:
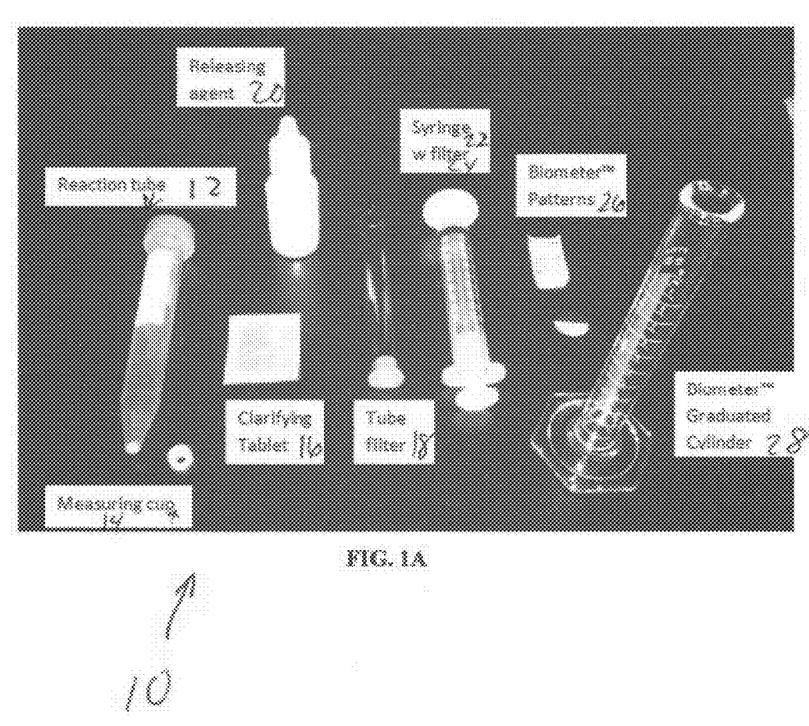
FIG. 1A shows Test Kit 1 for measuring the microbial population of a soil sample: a reaction tube, an open-ended measuring cup, a package containing a clarifying tablet, a tube filter, a vial of releasing agent, a syringe fitted with a syringe filter, patterns of opposing black and white Secchi disks and a SOIL BIOMETER™ turbidity tube.

FIG. 1A shows Test Kit 1 10 for measuring the microbial population of a soil sample: a reaction tube 12, an open-ended measuring cup 14, a package containing a clarifying tablet 16, a tube filter 18, a vial of releasing agent 20, a syringe 22 fitted with a syringe filter 24, patterns of opposing black and white Secchi disks 26 and a SOIL BIOMETER™ turbidity tube 28.

An alternative embodiment for measuring the microbial population of a soil sample includes: a reuseable sample collection device, a vial containing Granulated Chlorine Dioxide that can be solubilized with tap water, a vial of releasing agent, a fiberglass plug, patterns of opposing black and white Secchi disks and a SOIL BIOMETER™ turbidity tube.

Figure 1B:
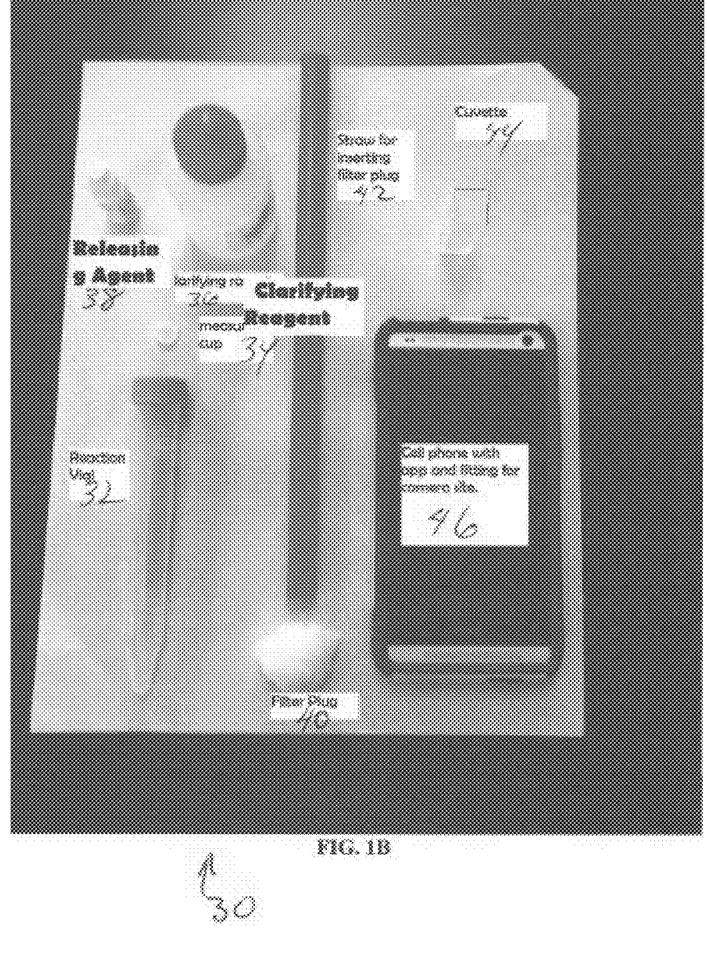
FIG. 1B shows Test Kit 2 for measuring the microbial population of a soil sample: a reaction tube, a sample collection cup; a vial containing Granulated Chlorine Dioxide that can be solubilized with tap water, a vial of releasing agent, a fiberglass plug, a cuvette for estimating turbidity, reflectance and/or transmittance with a Cell Phone Application.

Alternatively, as shown in FIG. 1B, the kit 30 can contain a reaction tube 32, a sample collection cup 34, a vial 36 containing Granulated Chlorine Dioxide that can be solubilized with tap water, a vial 38 of releasing agent, a fiberglass plug 40 with straw 42 to insert into reaction vial 32, a cuvette 44 for estimating turbidity, reflectance and/or transmittance with a Cell Phone 46 Application. In another version, the test kit contains the following reagents for measuring the microbial population of a soil sample: a 15 ml reaction tube containing 10 ml of a solution that contains clarifying and releasing reagents, a 3 ml syringe adapted to serve as punch plunger for delivering measured volume of solid soil, a hand held battery operated probe mixer, a filter plug and a Biometer Soil meter and pipette.

A. Soil Samples

Soil samples containing an earthy mix of minerals, air, water, and organic matter are disclosed. Soil samples can be liquids, such as compost extract or compost tea. Typically, soil samples for use in the described methods compose 2-5% of the testing reaction volume.

1. Compost

Composted organic matter and humus is a predominant component of the nutrient content of soil. Because solid compost is heavy and requires spreading for use as a fertilizer, many who use compost as fertilizer prefer to extract the nutrients and microbes in compost into water and apply the soluble compost extract by spraying. Solubilized compost sprayed directly onto plants can also have pesticidal activity which is attributed to the microbial content, thus eliminating the use of commercial pesticide. Compost extract can be fortified with other nutrients or microbes ("compost tea"), or diluted according to the requirements of the target crop. In some embodiments, methods for measuring the microbial content of soils can be used to determine the optimal concentration of solubilized compost for application to target crops. For example, solubilized composts can be diluted or concentrated from several billion parts/ml up to a million parts/mL, or less than a million parts per mL, based upon the microbial content of the sample. Based on the concentration of microbes the test can be used to determine the dilution factor that should be used for spraying of the extract or tea. It is also useful for evaluating compost extract conditions for optimal microbial content and nutritional additives used to increase microbial population of a compost extract.

2. Soil Microbes

Microbial life within the soil is a key factor in enhancing plant growth. Typically, the microbial diversity and biomass of a soil correlate with the ability of a soil to support the growth of plants. Soil microbes play an important role in the physical and chemical formation of soils. Microbes convert soil nutrients into forms that can be used by plants, control pathogens and bind the soil making it capable of retaining water and air. Thus, the microbial food chain in soil has been linked to crop yield and the presence of microbes within soil can be used as a marker for soil quality and fertility. At the bottom of the food chain are bacteria that provide food for protozoa like paramecia and amoeba, which are in turn grazed upon by nematodes that then feed larger animals such as earth worms and insects. In this process of grazing on bacteria which are rich in organic nitrogen, ammonia and nitrates are released for use by plants Bacteria are single-celled prokaryotic organisms, typically 1-8 micrometers in length. One gram of healthy soil typically contains $10^6$ to $10^8$ bacteria. The number of species of bacteria per gram of soil has been estimated as ranging between 2000 and 8.3 million (Gans, et al., Science, 309:1387-1390 (2005); Schloss and Handelsman, *PLoS Comput Biol.,* 2(7): e92. (2006)). The most abundant bacterial groups in soil samples from the Western Hemisphere were the Bacteroidetes, Betaproteobacteria and Alphaproteobacteria (Roesch, et al., *ISME J.,* 1:283-290 (2007)). Exemplary soil bacteria include *Nitrosomonas* spp., *Nitrobacter* spp., *Rhizobium* spp., *Bradyrrhizobium* spp., *Azotobacter* spp, *Bacillus* spp., *Azotobacter* spp., *Micrococcus* spp., *Achromobacter* spp., *Nitrosococcus* spp., *Pseudomonas* spp., *Serratia* spp., *Xanthomonas* spp. and *Clostridium*, spp.

Bacteria are responsible for biochemical transformations within soil and directly or indirectly provide nutrients for plant life. Important biochemical processes carried out by soil bacteria include ammonification (i.e., protein to ammonia), nitrification (i.e., ammonia to nitrites, to nitrates), denitrification (i.e., release of free elemental nitrogen) decomposition of cellulose and other carbohydrates, the symbiotic and non-symbiotic fixation of atmospheric nitrogen, as well as the oxidation and reduction of iron and sulfur compounds.

Bacteria also contribute to compost fertility by preventing pathogens through the production of bacteriocins and antibiotics, as well as by competition.

B. Collection and Reaction Vessels

The disclosed devices for obtaining soil samples include measuring vessels and other collection devices.

1. Collection and Measuring Devices

Different soil collection and measuring devices for use in obtaining samples from a variety of terrain and soil types are disclosed. A clean measuring cup with a known volume is disclosed. Typically, measuring cups or punches are used to obtain a known volume of soil because measurement of soil by volume substantially corrects for water content. A measuring device that contains a set volume between 200 ml and 800 ml of compost or soil is disclosed for use in obtaining a measured quantity of solid soil for a testing volume of 10 ml. In some embodiments the measuring device is not closed on the bottom, to facilitate release of the sample during shaking or agitation. In preferred embodiments the measuring device is a cup washer or punch with plunger. Cup washers can be manufactured in bulk and can be precisely sized to fit within the reaction vial. Cup washers having a bottom orifice that facilitates release of the sample during shaking, but is not so open as to preclude packing of consistent amounts of sample into the cup are disclosed. Cups and measuring devices can be disposable or can be formed of durable materials, such as plastic or rubber, to enable washing and reuse. A 3 ml syringe can be modified for use as a punch with plunger, allowing measurement of soil volume with a CV of <5% using the gradations on the syringe, with direct insertion into the reaction vial.

These devices may be reusable. Alternatively, the cups and measuring devices can be dissolved in water. In some embodiments, cups for measuring a defined amount of soil are readily dissolved upon contact with an aqueous solution. Dissolvable measuring cups release the measured amount of solid soil sample into solution upon dissolving. In further embodiments, dissolvable cups and measuring devices are constructed so as to incorporate reagents for use in the methods. Reagents incorporated into dissolvable measuring cups can include releasing agents such as CAPSIL®, clarification agents such as chlorine dioxide or CLOROX® Regular-Bleach, and anti-foaming agents such as simethicone.

Measurement of sample by volume corrects for soil water content. The volume of the cup washer is 0.21 ml, i.e. it holds 210 μl or 0.21 ml of water. For example, a cup on a plastic weigh boat is tared on a scale and packed with dry soil. 25 ul aliquots of DI were then added until water was detected emerging from the hole at the bottom. This exercise was performed with 2 different soil samples. The packed volume of the cup did not change during the addition of water. This demonstrated that a soil sample can hold more than 2× dry weight of soil before volume changes. See Table 3.

TABLE 3

Measuring volume compensates for water content of sample. Sample can hold more than 2x dry weight of soil before volume changes.

| μls water added | Weight Sample 1 | Weight Sample 2 | |
|---|---|---|---|
| 0 | 0.98 | 0.132 | |
| 25 | 0.103 | 0.155 | |
| 25 | 0.124 | 0.177 | |
| 25 | 0.146 | 0.201 | |
| 25 | 0.172 | 0.223 | |
| 25 | 0.197 | 0.257 | water seeped out bottom |
|  | 0.2197 |  | |
|  | 0.24 |  | water seeped out bottom |

Pipettes are disclosed for use in obtaining measured amounts of liquid soil samples. Preferred amounts of liquid soil samples are between 1 mL and 2 mL. A cap can also be used if cap volume is known.

2. Reaction Vials

Soil samples for use with the methods and compositions are solubilized within a reaction vessel or vial. In one embodiment, the tube has a diameter 17 millimeters and a length of 120 millimeters and holds a volume of 15 mL. In other embodiments the tube is sized to contain a volume of more than 15 mL, such as 50 mL, or more than 200 mL. An exemplary reaction vial is a polypropylene screw-cap vial, such as a conical centrifuge tube (e.g., Corning Life Sciences product No.: 352097). In some embodiments the cap of the vial is threaded to seal the entire circumference of the vial. The cap of the reaction vial can hold a volume of 1 or 2 mL, or more than 2 mL when completely filled. In a preferred embodiment, the reaction vial is made of a hydrophobic material with an inert inner surface and the reaction vial is transparent to facilitate visual inspection of the contents. The outer face of the vial can contain graduated marks to enable visual estimation of the volume of fluid within the vial. The reaction vial should be clean and free from microbial contaminants.

C. Agitation Devices

Devices for mixing soil solutions by agitation are disclosed. Equipment to facilitate shaking and agitation of solutions is commercially available from multiple sources. Commercially available portable battery-operated shakers, such as the "Robart shaker" are disclosed for use in the field setting. The battery operated version of the Robart shaker is small and incorporates easily into a portable field kit. Other commercially available shakers, such as those suitable for shaking small paint or nail polish samples, also disclosed. Electrically powered laboratory equipment for mixing fluids, such as the Vortex mixer, and ultrasonic equipment such as sonicators are also disclosed for use in the laboratory setting. A preferred method is to use of a battery operated vibrating wand, such as can be constructed using an ORAL® B children's tooth brush base with a plastic straw attached for penetrating the reaction vial.

D. Filters

Filters and filtration devices for separation and/or removal of particulate matter from the solubilized sample are disclosed. Devices for the filtration of particulates from a solution are well known in the art. Filters for use in the methods can be "coarse" filters (e.g., sized for the filtration of particles in excess of 100-1000 micrometers in diameter) or "fine" filters (i.e., sized for the filtration of smaller particles, such as those in excess of 5 micrometers in diameter). Compound filter devices that incorporate 2 or more filters of various sizes are available and have been successfully used, but are less than ideal because of their cost.

1. Coarse Filters

Filters to remove large particles are well known in the art. A coarse "pre-filter" can be a paper or fiberglass sieve, or a serum separator. Typically, a coarse filter has a sieve size of approximately 1000 micrometers. Coarse filters can be disk-shaped and sized to fit through the opening of the reaction vial. In a preferred embodiment, a disk-shaped coarse filter is sized to form a water-tight seal with the inner wall of the reaction vessel. The disk-shaped filter can be attached to one end of a tube of equal diameter. Solutions within the reaction vial can be filtered by insertion of the filtered end of the tube into the open end of the reaction vial. Coarse filters can be sized for the removal of soil particles and large organic debris. Filtration devices also include a French coffee press, a French coffee press fitted with a fine paper filter, or a coffee filter in a coffee funnel. Commercially available filtration devices, such as those available from Porex, and other serum filter-type devices are also disclosed.

2. Fine Filters

Fine filters with a sieve size smaller than coarse filters are disclosed. In a preferred embodiment a fine filter is a disposable syringe filter that provides a sieve size of about 5-20 micrometers, most preferably approximately 10 micrometers or approximately 5 micrometers. Syringe filters with different sieve sizes, designed to filter different sizes of microorganisms are disclosed.

In some embodiments a single filtration device is capable of multiple filtration steps. Preferred filters and sieves for use in the methods do not damage or otherwise disrupt microbes, do not bind microbes on the filter and do not exacerbate foaming.

In a preferred embodiment, a fiberglass (commercial insulation grade) plug of 250-750 mg replaces a series of filters. The fiberglass plug is inserted into the reaction vial after shaking and is slowly depressed using a straw or other device that allows the plug to be depressed while allowing fluid to pass through. The resulting eluent is substantially clear of cellulosic material. The advantage of fiberglass is its very low retention of microbes. Many commercial filter materials tested lowered microbial counts by 40-90%.

E. Turbidity, Reflectance and/or Transmittance Measuring Devices

Devices for measuring the turbidity, reflectance and/or transmittance of a solution are disclosed. Turbidity, reflectance and/or transmittance is a function of the cloudiness or haziness of a fluid, caused by the presence of suspended particulates. In preferred embodiments, the device for measuring turbidity, reflectance and/or transmittance is a narrow glass tube with a black and white Secchi disk pattern (or any pattern of colors that allows visual discrimination) at the base of the tube. Markings on the side of the tube enable reading the volume of the fluid at which the pattern becomes obscured by the fluid column within the tube. Other devices for measurement of turbidity, reflectance and/or transmittance known in the art, such as spectrophotometers or reflectometers, are also disclosed. In a preferred embodiment, the reflection of the filtrate is captured by a flash cell phone camera picture and analyzed by a phone app.

1. Secchi Disk

Figure 2:
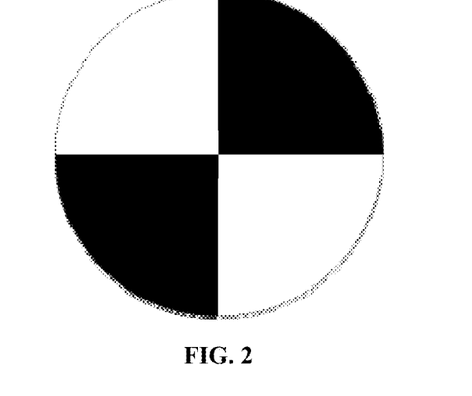
FIG. 2 shows the pattern of alternating black and white colored quadrants of a typical Secchi disk.

Secchi disks and similar devices are disclosed. Secchi disks for measuring turbidity include a disk of contrasting colors with four equally sized alternating black and white quadrants (see FIG. 2). The depth of fluid at which the pattern of the Secchi disk can be discerned by the naked eye provides a measure of the turbidity of the fluid above the disk. Other patterns of contrasting black and white shapes that can provide a visual reference of the turbidity of a fluid are known. In further embodiments, devices for use as Secchi disks contain alternating patterns of different contrasting colors. Secchi disks for use in the methods can be formed of printed plastic, or printed on paper or cardboard and sized according to the requirements of the turbidity tube.

2. Turbidity Tube

A preferred device for measuring turbidity in the field setting is a transparent, narrow, open-ended cylinder affixed to a support stand or platform. An exemplary tube, trademarked as the SOIL BIOMETER™ turbidity tube, is disclosed for use in the field setting (FIG. 1). The closed end of the tube can include a pattern of opposing colors that can be viewed from above the opening by looking down the length of the tube. In preferred embodiments the pattern of opposing colors is a Secchi disk (Preisendorfer, *Limnol. Oceanogr.* 31: 909-26 (1986)). In some embodiments the bottom of the tube is transparent and the Secchi disk or pattern is viewed by placing the tube over the pattern.

Figure 3:
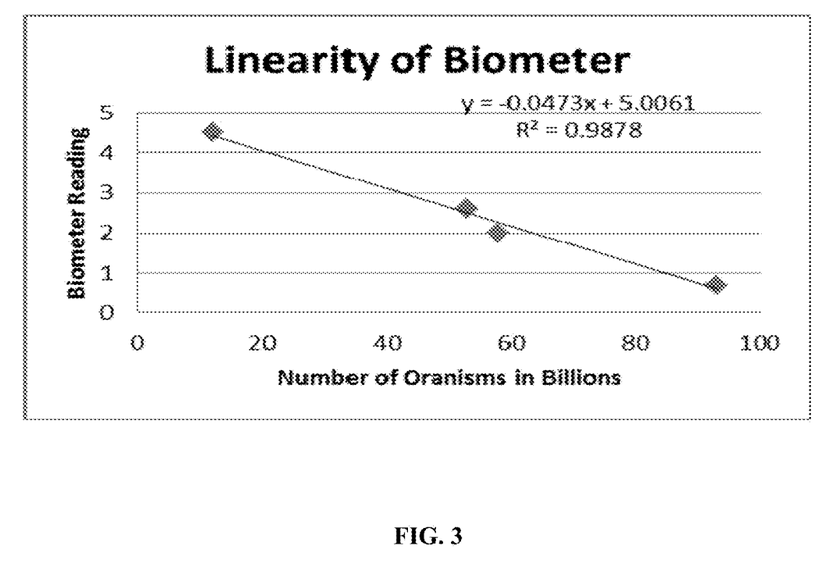
FIG. 3 is a scatter dot plot showing readings obtained from the SOIL BIOMETER™ (from 1 to 5) over numbers of organisms (in billions). $R^2$ for the line of the graph is 0.9878.

Turbidity tubes of different volumes are disclosed. In a particular embodiment the cylindrical tube has a volume of 10 mL, similar to a 10 ml glass graduated cylinder. In another embodiment the cylindrical tube has a volume of 25 mL. The volume of fluid required to obscure the pattern correlates with the number of bacteria within the solution. The height of the fluid column within the tube (i.e., the volume of fluid) at which the pattern disappears is inversely correlated with microbial count. An exemplary list of bacterial counts correlated with the turbidity of fluid in the SOIL BIOMETER™ turbidity tube is provided in FIG. 3.

The outer side of the tube includes markings that allow for calibration and measurement of turbidity in a solution by the height of fluid within the tube. Solutions containing known numbers of particles of a known size (i.e., 0.1-20 micrometers, most preferably approximately 5 micrometers) are also disclosed for use as standards to calibrate the device.

3. Other Devices for Measuring Turbidity, Reflectance and/or Transmittance.

Automated devices, including spectrophotometers, nephelometers and reflectometers are disclosed for the measurement of the turbidity of solutions. Absorbance/Transmittance is routinely measured to estimate the concentration of bacterial cultures in the laboratory. Commercially available standards, such as the Mc Farland standards, are disclosed for the quantitation of bacterial suspensions. Standards can be used as a reference to adjust the turbidity so that the number of bacteria will be within a given range.

EXAMPLES

Example 1

Methods for Measurement of Bacteria in Soil

Methods to assess turbidity, reflectance and/or transmittance without need for large laboratory equipment, such as a spectrophotometer, have been established. The methods remove soil particles and pigments which contribute to turbidity, reflectance and/or transmittance. The methods also overcome problems associated with microbes that are firmly attached to the soil particles and do not go into solution. The preparation steps covered in this patent can also be used to facilitate the measurement of soil analytes and biomass in the laboratory and incorporated in this patent.

Methods and Materials

The microbial content of soil was estimated using the equipment and methods of the SOIL BIOMETER™ test kit (FIG. 1), according to the following instructions:

1. Pack the measuring cup with a known amount of coarse filtered soil (see Table 2) or for compost extract/tea measure out 1 mL using the disposable pipettes. Alternatively, 2 capfuls or 2 mL of a liquid sample can be used.
2. Add 1 drop of Releasing Agent
3. Add 1 Clarifying Tablet or 5 drops of saturated Chlorine dioxide
4. Fill reaction vial to 10 mL line with water.
5. Shake in Robart shaker for 1 minute.
6. Remove cap from tube and allow to settle for 10-30 seconds.
7. While the tube is settling insert the tube filter onto the reaction vial, then slowly press in down into the tube. Filtered fluid will move into the tube filter. For some samples a second tube filter may be necessary.
8. Place the 5 or 10 ul syringe filter on the syringe, remove the plunger and set the syringe on the SOIL BIOMETER™ turbidity tube.
9. Pour the fluid in the reaction vial into the 10 mL syringe attached to the filter.
10. Insert the plunger till all fluid is expressed into the SOIL BIOMETERT™. Place the SOIL BIOMETER™ turbidity tube over the SOIL BIOMETER™ pattern.
11. Look into the SOIL BIOMETER™ turbidity tube and using a disposable pipette remove fluid until the black/white divide becomes visible. It may be necessary to use the pipette to remove some of the foam from the surface. Estimate the number of microbes/ml less than 5 µm in size according to Table 1.
12. The SOIL BIOMETER™ reading is approximately linear for readings between 1.5 and 7 (see FIG. 3). If the sample reads less than 1.5, an accurate reading can be obtained by dilution in water and multiplying results by the dilution factor (e.g., if diluted by adding an equal volume of water, multiply results by 2).

Results

The test was performed 16 times on a single sample of compost using the described steps 1-12 (above). The 16 tests were performed over the course of one week by 2 different technicians. Following each reading from the SOIL BIOMETER™ a sample was removed from the tube and immediately evaluated for the number of microbes using a hemocytometer. The coefficient of variation, CV value (i.e., the standard deviation divided by the average), was 24% for cell count numbers determined using the hemocytometer, as compared to only 5% for the 16 readings using the SOIL BIOMETER™ tube. The greater accuracy for readings obtained using the SOIL BIOMETER™ tube reflects the fact that the SOIL BIOMETER™ method measures billions of cells, whereas the hemocytometer count because it dilutes samples by a factor of approximately 1 million is sampling a much smaller sample and smaller samples can be to produce less accuracy and precision.

The results indicated that approximately 0.2 ccof compost diluted in 10 ml yielded sufficient bacterial turbidity for testing using the described steps 1-12 (above). The sample volume method is not significantly affected by the soil moisture content.

Example 2

Methods for Measurement of Bacteria in Soil
Methods and Materials

1. Pack the punch with plunger 0.33 cc of coarse filtered soil (see Table 2) or for compost extract/tea measure out 1-2 mL using the disposable pipettes.

2. Add to reaction vial that contains clarifying and releasing agent.
3. Insert vibrating wand and turn on for 15 seconds.
4. Remove cap from tube and insert the tube filter onto the reaction vial, then slowly press in down into the tube using the straw.
5. Pour the filtrate into the SOIL BIOMETER™ turbidity tube over the SOIL BIOMETER™ pattern.
6. Look into the SOIL BIOMETER™ turbidity tube and using a disposable pipette remove fluid until the black/white divide becomes visible. It may be necessary to use the pipette to remove some of the foam from the surface. Estimate the number of microbes/ml less than 10 μm in size according to Table 1.

Results:
20 replicates gave an average Biometer reading 2.5 and CV of 3.1%.

Particulates affecting turbidly are only substantially removed with a 5 or 10 micrometer filter or the composite filter that the 500 mg fiberglass plug provides. A 5 μm filter preferentially selects for bacteria. Protozoa and nemotodes are best included by the use of 10 μm filter. Other soil organisms that are generally too large to pass through this filter will not be counted and the estimated quantities reflect the quantity of soil bacteria that are smaller than 5-10 micrometers. Fungi were not observed when counting the bacteria in a sample, even though they are small enough to pass through the filter and it is likely that fungi are destroyed during the preparation phase of the test. The population density of fungi is routinely estimated by the chiten or erogosterol content of a sample. The filtrate will provide sample that can be tested for ergosteroy and/or chiten by colorimetric chemical assay or immunoassay.

Both methods had levels of precision of approximately 3%. This level of precision compares most favorably with a field spectrophotometer and it has the advantage of not requiring power or calibration (see Tables 3 and 4).

TABLE 3

Weights of 20 compost samples measured by packing a cap washer.
Weight of compost in washer (grams)

| | | | |
|---|---|---|---|
| 0.107 | 0.102 | 0.106 | 0.113 |
| 0.118 | 0.144 | 0.1 | 0.077 |
| 0.111 | 0.073 | 0.071 | 0.112 |
| 0.144 | 0.062 | 0.105 | 0.104 |
| 0.091 | 0.108 | 0.113 | 0.103 |

TABLE 4

Average numbers of bacterial cells counted by SOIL BIOMETER™ and hemocytometer.

| | Cell Count | |
|---|---|---|
| | SOIL BIOMETER™ | Hemocytometer |
| 1 | 69 | 58.5 |
| 2 | 61 | 61.5 |
| 3 | 55.5 | 54.5 |
| 4 | 53.5 | 65.5 |
| 5 | 62.5 | 71 |
| 6 | 63.5 | 81 |
| 7 | 59.5 | 88.5 |
| 8 | 58.5 | 83.5 |
| 9 | 60 | 61.5 |
| 10 | 72.5 | 65.5 |
| 11 | 68.5 | 69.1 |

TABLE 4-continued

Average numbers of bacterial cells counted by SOIL BIOMETER™ and hemocytometer.

| | Cell Count | |
|---|---|---|
| | SOIL BIOMETER™ | Hemocytometer |
| Av | 62.2 | 69.1 |
| StD | 5.84 | 11.5 |
| CV | 9% | 17% |

TABLE 5

Comparison of tests used to estimate microbial life of the soil

| Test | Measures | Time required | Instrumentation | Level of expertise |
|---|---|---|---|---|
| Direct Count | All microbes | 1 hour | Microscope, Sonicator | Laboratory technician |
| DAPI and other staining techniques | Metabolically active bacteria | hours | Laboratory | Laboratory technician |
| Culturing | 1-12% | 12 weeks | Soil Microbiology Laboratory | Laboratory technician |
| ATP content | All? | day | Laboratory equipment | Laboratory technician |
| Chloroform-fumigation method | Microbial C and N | week | Organic laboratory | Laboratory technician |
| Respiration | $CO_2$ | day | Laboratory equipment | Laboratory technician |
| PCR | DNA | week | DNA sequencing capability | Laboratory technician |
| SOIL BIO-METER™ | Total bacteria | 3 minutes | Field kit | Anyone |

Example 3

Effects of CAPSIL® on Bacterial Count

Test 4 method was performed with and without CAPSIL®. Biometer reading without CAPSIL® was 3.5, with CAPSIL® 2.5. Identical results were obtained with Tween 20 as solubilizer at a 0.1% concentration. Microscopic analysis confirmed the increased release.

Before counting or culturing soil bacteria, they must be separated from soil particles by vigorous shaking or sonication and/or detergent. Releasing microbes from soil is accomplished by vigorous shaking and the use of a mild detergent agent such as CAPSIL®. A requirement of the releasing agent is that it only causes minimal foaming and does not interfere with turbidity, reflectance and/or transmittance and filtration. It should also be stable in a packaged and ready to use form. Release by sonication is not easily adaptable to field conditions and shaking alone requires a long time until a stable number is released. One should avoid solubilizing agents that can damage microbial membranes.

Materials and Methods

Two samples of 10 grams of compost were brought up to 100 mL in tap water that had been de-chlorinated by allowing it to stand for more than 2 days in an open container. CAPSIL® was added to a final concentration of 0.01% in one sample. The other (control) sample was untreated. Both samples were stirred overnight. The sample treated with CAPSIL® was tested 3 and 6 hours following addition of the CAPSIL®. The control sample was not tested as it had previously been determined that optimal microbe harvest was at 20-48 hours. The next day both samples were evaluated in duplicate by SOIL BIOMETER™ reading and manual count of microbes using a hemocytometer.

Results

Both samples gave the same reading for turbidity (1.3) using the SOIL BIOMETER™ tube. The addition of CAPSIL® to a final concentration of 0.01% did not affect bacterial growth over the course of 24 hours. CAPSIL® supplemented compost extract preparations had twice as many bacteria after 16 hours (O/N) as control extract. CAPSIL® contains a non-foaming agent and is certified for use as an environmentally acceptable agricultural spray.

In conclusion, addition of CAPSIL® did not have an adverse effect on microbes. Data are shown in Table 6, below.

TABLE 6

Numbers of microbes measured by SOIL BIOMETER ™ with or without the presence of CAPSIL ®, at different time points

| Sample | Biometer Reading | Dilution | Total Count | Squares Counted | Average No. | Microbes/ml |
|---|---|---|---|---|---|---|
| Compost | 1.3 | 1/3 | 120 | 4 | 118 | 3.54E+08 |
| O/N | 1.3 | 1/3 | 116 | 4 | | |
| CAPSIL ® | 1.3 | 1/3 | 126 | 4 | 127 | 3.81E+08 |
| O/N | 1.3 | 1/3 | 128 | 4 | | |
| CAPSIL ® 3 hr | 1.3 | 1/3 | 120 | 2 | 117.5 | 3.53E+08 |
| | 1.3 | 1/3 | 115 | 2 | | |
| CAPSIL ® 6 hr | 1.5 | 1/4 | 109 | 4 | 111 | 4.44E+08 |
| | 1.5 | 1/4 | 113 | 4 | | |

Example 4

Effects of Differences in Bacterial Cell Size

Cultures of two different-sized bacteria species, *Serratia* spp. and *Bacillus megaterium* were measured using the SOIL BIOMETER™ turbidity tube. Despite the large difference in size between these two species, the estimation of count using the SOIL BIOMETER™ was not statistically different to the count obtained by classical serial dilution plating methods, indicating that the size and shape of the microbes does not substantially affect measurement.

Example 5

Measurement of Soil Nitrogen Levels Using the SOIL BIOMETER™ Turbidity Tube

Measurement of fluid turbidity using the SOIL BIOMETER™ turbidity tube can be applicable to samples other than soil/compost. In some embodiments of the methods, the eluent can be analyzed for nitrogen using any of the available methods for determination of protein, nitrates or nitrites, or amino sugars.

Methods disclosed for the SOIL BIOMETER™ system can be used for the bicinchoninic acid assay (BCA assay) for determining the total concentration of protein in a solution. The BCA assay is easy to carry out and the stability of the reagents and the tests insensitivity to interfering substances such as detergents and pH.

TABLE 7

Pierce and SOIL BIOMETER ™ BCA test results for BSA protein standards.

| BSA Std (mg/ml) | SOIL BIOMETER ™ BCA | Pierce Standards BCA |
|---|---|---|
| 0 | 1.01 | 0.069 |
| 0.031 | 0.11 | 0.087 |
| 0.062 | 0.118 | 0.106 |
| 0.125 | 0.141 | 0.14 |
| 0.25 | 0.186 | 0.195 |
| 0.5 | 0.243 | 0.287 |
| 1 | 0.382 | 0.501 |
| 2 | 0.576 | 0.8 |

Nitrogen content in the compost samples was measured in filtrate using the BCA assay. Values of 0.137 and 0.121 corresponded to the SOIL BIOMETER™ and Pierce BCA values, respectively. The concentration of Nitrogen in the sample was determined according to the corresponding standard values presented in Table 7 as being 0.141 milligrams per mL of eluent.

In conclusion, the methods for preparation of soil samples can also be used to determine the Nitrogen content of soil samples, for example by using the BCA assay. The data indicate that the lysis of microbes will likely greatly increase this concentration. These data can be used to provide an estimate of the total nitrogen that will be available to plant life.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of determining the microbial population of a sample of soil or compost, comprising
   (a) measuring a volume of the sample;
   (b) solubilizing microbes in the sample in a known volume of water comprising salt and/or detergent to form a microbial solution, separate from soil;
   (c) compensating for pigments in the microbial solution, if necessary, by adding a bleaching agent;
   (d) filtering the microbial solution through a filter allowing passage only of microorganisms and not soil to produce a filtrate comprising microorganisms approximately five microns in diameter or less;
   (e) measuring turbidity, reflectance or transmittance of the filtered microbial solution; and
   (f) determining the number of microbes in solution based upon the turbidity, reflectance or transmittance measurement by comparison to standard values of microbes based upon reference turbidity, reflectance or transmittance values.

2. The method of claim 1 wherein the sample of soil or compost is compost extract, compost tea or other earthy material.

3. The method of claim 1 wherein the microbes are solubilized by shaking the sample and water to form a solution.

4. The method of claim 3 wherein shaking the solution comprises shaking for 5 seconds to 1 minute using a portable automated shaker device or shaking by hand up to 30 minutes.

5. The method of claim 3 further comprising adding a detergent to the sample to enhance solubilization of the microbes.

6. The method of claim 5 wherein the detergent is polyether modified polysiloxane added to a concentration of 0.2% or polysorbate 20 to 0.1%.

7. The method of claim 1 wherein compensating for pigments in the microbial solution comprises bleaching the pigments in the sample or reading absorbance at a wavelength at which the pigments do not absorb.

8. The method of claim 7 wherein bleaching the pigments in the sample is by the addition of chlorine dioxide or a formulation comprising sodium hypochlorite, sodium chloride, sodium carbonate, sodium hydroxide and sodium polyacrylate.

9. The method of claim 8 wherein chlorine dioxide is added to a concentration of 0.08 mg/mL or 75 ppm.

10. The method of claim 1 wherein most of the color and cellulosic material is removed from the sample for analysis of solubilized microbes by methods requiring a non-pigmented sample.

11. The method of claim 1 wherein filtering the microbial solution comprises using different filter sizes to divide the microbial population by size, and estimating the numbers of microbes at each size level.

12. The method of claim 11 wherein a filter having a pore size of between 100 and 1000 micrometers is used, followed by a 5 micrometer filter.

13. The method of claim 11 wherein the filter is a fiberglass plug of between 200 and 600 mg for a standard 15 ml centrifuge tube holding 10 ml of reaction solution.

14. The method of claim 1 wherein measuring the turbidity of the filtered microbial solution is by spectrophotometry, nephalometer or reflectometry.

15. The method of claim 1 wherein measuring the turbidity of the filtered microbial solution is by use of a device that correlates color with turbidity measurements based upon standardized controls, and a turbidity tube.

16. The method of claim 1 wherein the turbidity, reflectance and/or transmittance of the filtered microbial solution is measured using a portable camera with a software application to calculate the measurement.

17. The method of claim 16 wherein the portable camera is a smart phone or wrist watch.

18. A kit comprising the reagents and devices as in any of claims 1-17.

19. The kit of claim 18 comprising one or more of a syringe, a syringe filter with a 5 micrometer sieve size, a tube filter with a 100 micrometer sieve size, filter or fiberglass plug, a measuring cup with a capacity of up to 100 milligrams of soil when fully packed, one or more vials or packages containing detergent releasing agent and/or solubilizing agent, a bleaching agent liquid, granules or tablet, a reaction vial, a pipette and a Secchi disk.

20. The kit of claim 18 further comprising a portable automated shaker device.

21. The kit of claim 19 further comprising a transparent 10 ml glass measuring cylinder, having one end of the cylinder open and the opposing end closed and connected to a support stand, wherein the closed end is transparent or can include a pattern of opposing colors that is visible from above by looking through the open end of the cylinder, or a separate color schedule, and the transparent cylinder includes markings to allow measurement of the fluid within the cylinder by the height of the fluid column.

22. The method of claim 13 wherein the filter is a fiberglass plug of 500 mg.

* * * * *